(12) United States Patent
Weber

(10) Patent No.: US 11,357,623 B2
(45) Date of Patent: Jun. 14, 2022

(54) DECALCIFYING HEART VALVE

(71) Applicant: Boston Scientific Scimed, Inc., Maple Grove, MN (US)

(72) Inventor: Jan Weber, Maastricht (NL)

(73) Assignee: Boston Scientific Scimed, Inc., Maple Grove, MN (US)

( * ) Notice: Subject to any disclaimer, the term of this patent is extended or adjusted under 35 U.S.C. 154(b) by 482 days.

(21) Appl. No.: 15/954,845

(22) Filed: Apr. 17, 2018

(65) Prior Publication Data

US 2018/0228602 A1     Aug. 16, 2018

Related U.S. Application Data

(63) Continuation of application No. 13/708,292, filed on Dec. 7, 2012, now Pat. No. 9,987,130.

(60) Provisional application No. 61/569,961, filed on Dec. 13, 2011.

(51) Int. Cl.
*A61F 2/24* (2006.01)
*A61L 31/10* (2006.01)
*A61L 31/14* (2006.01)

(52) U.S. Cl.
CPC .......... *A61F 2/2412* (2013.01); *A61F 2/2415* (2013.01); *A61F 2/2418* (2013.01); *A61L 31/10* (2013.01); *A61L 31/145* (2013.01); *A61F 2220/005* (2013.01); *A61F 2220/0058* (2013.01); *A61F 2220/0075* (2013.01)

(58) Field of Classification Search
CPC .. A61F 2/24; A61F 2/27; A61F 2/2412; A61F 2/2415; A61F 2/2418; A61L 31/145
See application file for complete search history.

(56) References Cited

U.S. PATENT DOCUMENTS

| | | |
|---|---|---|
| 3,867,329 A | 2/1975 | Halpern |
| 4,976,733 A | 12/1990 | Girardot |
| 6,254,635 B1 | 7/2001 | Schroeder et al. |
| 7,364,585 B2 | 4/2008 | Weber |
| 7,510,575 B2 | 3/2009 | Spenser et al. |
| 7,727,273 B2 | 6/2010 | Stinson et al. |
| 8,114,153 B2 | 2/2012 | Holman et al. |

(Continued)

FOREIGN PATENT DOCUMENTS

| | | |
|---|---|---|
| CA | 2860829 | 8/2016 |
| CN | 102202610 | 9/2011 |

(Continued)

OTHER PUBLICATIONS

Asmatulu, et al., "Drug-Carrying Magnetic Nanocomposite Particles for Potential Drug Delivery Systems," Journal of Nanotechnology, vol. 2009, Article ID 238536 (6 pages).

(Continued)

*Primary Examiner* — Christopher D. Prone
(74) *Attorney, Agent, or Firm* — Pauly, DeVries Smith & Deffner LLC

(57) ABSTRACT

Vascular valve systems for treating calcified vascular vessel valves by delivery of one or more calcium chelating agents are described. The vascular valve systems can include an expandable stent, a valve, and a material layer. The material (Continued)

layer includes a hydrogel, calcium chelating agent, and an acidifying agent. Methods of making the vascular valve systems are also described.

12 Claims, 8 Drawing Sheets

(56) References Cited

U.S. PATENT DOCUMENTS

| | | | |
|---|---|---|---|
| 2002/0090725 A1* | 7/2002 | Simpson | D01F 1/10 435/402 |
| 2002/0144757 A1 | 10/2002 | Craig et al. | |
| 2003/0018380 A1 | 1/2003 | Craig et al. | |
| 2003/0028243 A1 | 2/2003 | Bates et al. | |
| 2003/0065292 A1* | 4/2003 | Darouiche | A61L 29/16 604/265 |
| 2003/0077200 A1 | 4/2003 | Craig et al. | |
| 2003/0139801 A1 | 7/2003 | Sirhan et al. | |
| 2004/0143317 A1 | 7/2004 | Stinson et al. | |
| 2005/0048124 A1* | 3/2005 | Sarangapani | A61K 33/38 424/486 |
| 2005/0070990 A1 | 3/2005 | Stinson et al. | |
| 2006/0069069 A1 | 3/2006 | Kajander et al. | |
| 2006/0115514 A1 | 6/2006 | Gengrinovitch | |
| 2006/0195183 A1* | 8/2006 | Navia | A61F 2/2457 623/2.18 |
| 2007/0067022 A1 | 3/2007 | Case et al. | |
| 2008/0275318 A1 | 11/2008 | Lastovich et al. | |
| 2011/0111033 A1* | 5/2011 | Stover | C08L 5/04 424/487 |
| 2011/0135726 A1 | 6/2011 | Munro et al. | |
| 2012/0150142 A1 | 6/2012 | Weber et al. | |
| 2013/0150957 A1 | 6/2013 | Weber et al. | |

FOREIGN PATENT DOCUMENTS

| | | |
|---|---|---|
| CN | 104220104 | 2/2017 |
| EP | 1057460 | 12/2000 |
| EP | 2793969 | 9/2016 |
| JP | 2001000460 | 1/2001 |
| JP | 2002501787 | 1/2002 |
| JP | 2003518984 | 6/2003 |
| JP | 2009533168 | 9/2009 |
| WO | 9938544 | 9/1999 |
| WO | 0149213 | 7/2001 |
| WO | 2007121072 | 10/2007 |
| WO | 2010049160 | 5/2010 |
| WO | 2013090145 | 6/2013 |

OTHER PUBLICATIONS

"Communication Pursuant to Rules 161(1) and 162 EPC," for European Patent Application No. 12810463.5, dated Oct. 6, 2014 (2 pages).
"Decision of Rejection," for Japanese Patent Application No. 2014547316 dated Nov. 8, 2016 (7 pages) with English summary.
"First Office Action," for Chinese Patent Application No. 201280069544.2, dated Jun. 9, 2015 (6 pages).
"International Preliminary Report on Patentability," for PCT/US2012/068495, dated Jun. 17, 2014 (6 pages).
"International Search Report and Written Opinion," for PCT/US2012/068495, dated Apr. 22, 2013 (8 pages).
Jun, et al., "In situ Gel Forming Stereocomplex Composed of Four-Arm PEG-PDLA and PEG-PLLA Block Copolymers," Macromolecular Research, vol. 16, No. 8, pp. 704-710, (2008).
Krishna, et al., "Comparative Evaluation fo Chelating Gels-Indigenously Developed Vs Commercially Available," Trends in Biomaterials and Artificial Organs, vol. 16, No. 1, pp. 21-24 (2002).
Kumar, et al., "Polyanhydrides: an overview," Advanced Drug Delivery Reviews, vol. 54, pp. 889-910, (2002).
Nguyen, et al., "Biodegradable oligo(amidoamine/B-amino ester) hydrogels for controlled insulin delivery," The Royal Society of Chemistry: Soft Matter, vol. 7, pp. 2994-3001,(2011).
"Notice of Allowance," for Canadian Patent Application No. 2860829 dated Feb. 24, 2016 (1 page).
"Office Action," for Canadian Patent Application No. 2,860,829, dated Jun. 30, 2015 (4 pages).
"Office Action," for Japanese Patent Application No. 2014-547316 dated Mar. 22, 2016 (8 pages) with English translation.
"Office Action," for Japanese Patent Application No. 2014-547316, dated Jul. 1, 2015 (6 pages) with translation.
"Response to Communication Pursuant to Rule 161(1) and 162 EPC," for European Patent Application No. 12810463.5, dated Oct. 6, 2014 and filed with the EPO Mar. 5, 2015 (54 pages).
"Response to Examiner's Report," for Canadian Patent Application No. 2,860,829, dated Jun. 30, 2015 and filed with the CPO Dec. 30, 2015 (30 pages).
Schetsky, "Shape Memory Alloys," Encyclopedia of Chemical Technology (3rd ed.), John Wiley & Sons, vol. 20, pp. 726-736, (1982).
"Second Office Action," for Chinese Patent Application No. 201280069544.2, dated Dec. 30, 2015.
Tan, et al., "Injectable, Biodegradable Hydrogels for Tissue Engineering Applications," Materials, vol. 3, pp. 1746-1767, Mar. 10, 2010.

\* cited by examiner

DECALCIFYING HEART VALVE

This application is a continuation of U.S. Pat. No. 9,987,130, issued Jun. 5, 2018, which claims the benefit of U.S. Provisional Patent Application No. 61/569,961, filed on Dec. 13, 2011, the entire contents of all of which are herein incorporated by reference.

TECHNICAL FIELD

This invention relates to vascular valve systems, more particular to vascular valve systems that can remove calcification.

BACKGROUND

Without wishing to be bound by theory, it is believed that placing an artificial heart valve by a transcatheter aortic-valve implantation ("TAVI") procedure can lead to a higher risk for stroke, resulting from pieces of calcification being released from the original heart valve. However, release of calcium deposits often may not occur during the procedure, but during the days following the procedure. This can occur when calcium deposits are broken into many pieces during the procedure, but are not immediately released from the initial valve surfaces. Instead, small pieces of calcium deposits can hang loose and be released at a later time due to continuous movement of the valve. For this reason, treating the calcium deposits before they are released into the blood stream can be important to the long term success of a transcatheter aortic-valve implantation procedure.

SUMMARY

In one aspect, the disclosure features a vascular valve system including an expandable stent that includes an outer surface and a lumen; a valve that includes a plurality of leaflets; and a layer disposed on at least a portion of the outer surface of the stent. The valve is disposed within the lumen and coupled to the expandable stent. The layer includes a hydrogel, a calcium-chelating agent, and an acidifying agent.

In another aspect, the disclosure features a vascular valve system including an expandable stent that includes an outer surface and a lumen; a valve comprising a plurality of leaflets; and a permeable housing disposed on one or more leaflets, or around a portion of the outer surface of the stent, or both. The valve is disposed within the lumen and coupled to the expandable stent. The disclosure further features a method of replacing a heart valve, including implanting the vascular valve system, and injecting a solution comprising a hydrogel, a calcium-chelating agent, and an acidifying agent into the permeable housing.

Embodiments of the above-mentioned aspects can have one or more of the following features.

In some embodiments, the valve includes at least two leaflets (e.g., three leaflets). The valve can include porcine pericardium or a polymeric material. The valve can be attached to the stent with a plurality of sutures. The layer can be disposed around a circumference of the valve. The hydrogel can be in the form of a plurality of fibers, a coating, a sheet, a film, or a viscous liquid. In some embodiments, the hydrogel is selected from the group consisting of oligo (amidoamine/β-amino ester), methyl cellulose, collagen, gelatin, chitosan, hyaluronic acid, chondroitin sulfate, alginate, agar, agarose, fibrin, albumin, polyethylene glycol, polyethylene oxide, polyvinyl alcohol, poly(propylene fumarate), oligo(polyethylene glycol) fumarate, poly(N-isopropylacrylamide), polypropylene oxide, poly(aldehyde guluronate), polylactic acid, polyglycolic acid, poly(lactic-co-glycolic) acid, polyanhydride, combinations thereof, and copolymers thereof.

In some embodiments, the calcium-chelating agent is selected from the group consisting of ethylene diamine tetraacetic acid, phosphonates, 1,2-bis(2-aminophenoxy) ethane-N,N,N',N'-tetraacetic acid, ethylene glycol-bis(2-aminoethylether)-N,N,N',N'-tetraacetic acid, trans-1,2-cyclohexanediaminetetraacetic acid, N-hydroxyethylenediaminetriacetic acid, diethylenetriaminepentaacetic acid, and glycine. The calcium-chelating agent can be covalently bound to the hydrogel. The hydrogel can include from one percent to ten percent by weight of the calcium-chelating agent.

In some embodiments, the acidifying agent is selected from the group consisting of citric acid, ascorbic acid, acetic acid, lactic acid, and any combination thereof. The acidifying agent can be covalently bound to the hydrogel. The hydrogel can include from 0.5 percent to 20 percent by weight of the acidifying agent.

In some embodiments, the hydrogel is crosslinkable. The hydrogel can include polyethylene glycol diacrylate and poly(ethylene glycol) dimethacrylate.

In some embodiments, the permeable housing is disposed around a circumference of the valve. A hydrogel, a calcium-chelating agent, and an acidifying agent can be disposed within the housing. The vascular valve system can further include a layer disposed on at least a portion of the outer surface of the stent, the layer including a hydrogel, a calcium-chelating agent, and an acidifying agent.

Embodiments and/or aspects can provide one or more of the following advantages.

In some embodiments, the hydrogel can immobilize loose calcium fragments, while the calcium chelators can subsequently chelate (e.g., bind to) and solubilize the fragments, such that the chelated calcium can be removed in a body fluid. In some embodiments, when the valve system includes hydrogel fibers, the fibers can provide a deformable open structure that can conform to a space around the valve, while acting at the same time as a network in which large debris can be captured. The open structure can allow access to plasma and endothelial progenitor cells, which can assist in covering the replaced native valve.

In some embodiments, when the hydrogel is in the form of a coating, sheet, or film, the coating, sheet, or film can be continuous or discontinuous, have perforations at regular or irregular intervals and of any size and/or shape, and/or can have variable thickness from one region to another.

In some embodiments, the film, coating, or sheet can provide increased storage volume for chelators, compared to a fiber network. In some embodiments, a film can allow for dissolution and removal of calcium deposits by, for example, chelation of the calcium deposits.

In some embodiments, when the hydrogel is in the form of a liquid, a larger volume of a liquid can be delivered compared to a hydrogel film, coating, or sheet, or a fiber system. A liquid can provide greater adaptability (e.g., can conform to) to open volumes around the implanted valve.

In some embodiments, the housing or the hydrogel layer can span the thickness of the valve, and when implanted, can fully cover a native valve that is now positioned between a body vessel and the heart valve system.

The details of one or more embodiments of the invention are set forth in the accompanying drawings and the descrip-

DESCRIPTION OF DRAWINGS

FIG. 5A is a magnified view of a stent strut.
FIG. 5B is a magnified cross-sectional view of a stent strut.

DETAILED DESCRIPTION

Figure 1:
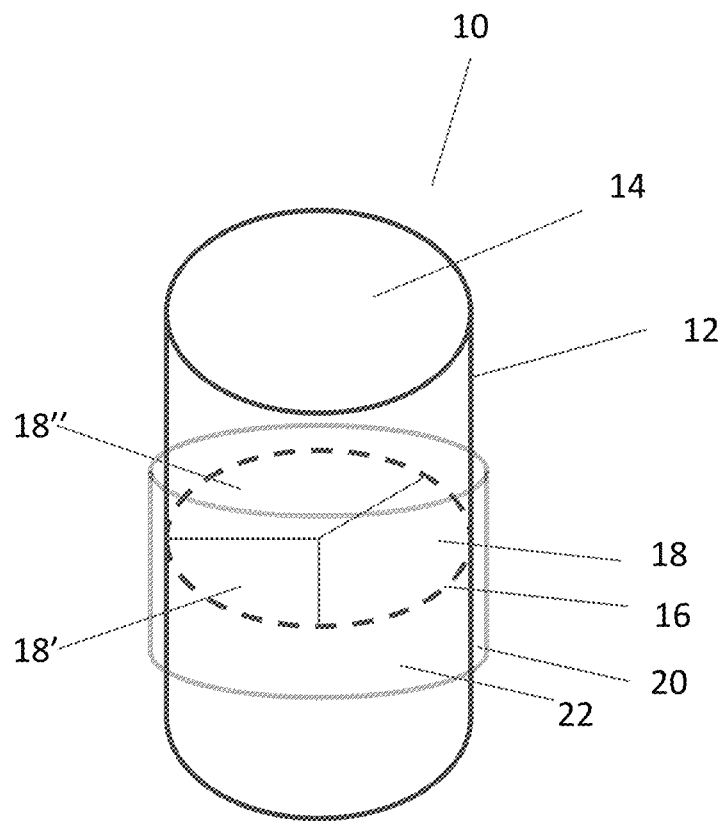
FIG. 1 shows an embodiment of a vascular valve system.

Referring to FIG. 1, in some embodiments, implantable heart valve systems 10 include a tubular expandable stent, which includes an outer surface 12 and a lumen 14. The lumen can include a valve 16 that has a plurality of leaflets (e.g., 18, 18', 18") attached to the expandable stent via, for example, a plurality of sutures, a glue, or by heat bonding (e.g., laser welding). Valve 16 can be formed of, for example, porcine pericardium or a polymeric material. A soft hydrogel 20 loaded with calcium chelators (e.g., calcium chelating agent) 22 can be disposed on the outside of implantable heart valve systems. The hydrogel can immobilize loose calcium fragments, while the calcium chelators can subsequently chelate (e.g., bind to) and solubilize the fragments, such that the chelated calcium can be removed in a body fluid.

Figure 2:
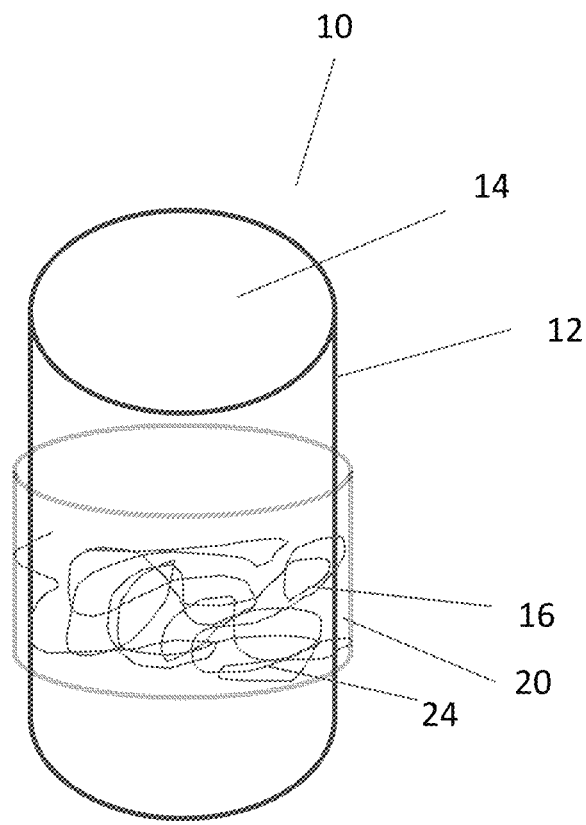
FIG. 2 shows an embodiment of a vascular valve system.

In some embodiments, referring to FIG. 2, the hydrogel coating can include a network of fibers 24 (e.g., electrospun fibers) positioned on the outside of the valve housing. Chelators 22 (not shown) can form part of the fibers, and/or the space between the fibers can be filled with chelators. For example, ion-exchange/chelating functionalities can be incorporated into a polymer matrix of the hydrogel or hydrogel fibers by polymerization, co-polymerization, and/or grafting. As another example, chelating agents such as ethylenediamine tetraacetic acid (EDTA) and amino acids (e.g., aspartic acid, glutamic acid, molecules containing aspartic and/or glutamic acid such as poly(aspartic acid-co-aminocarboxylic acid), alkylamine-modified polyaspartic acid) can be encapsulated and uniformly dispersed within the outer hydrogel coating.

The hydrogel coating can include acidic functionalities, such that at an ion-exchange (chelating) polymer/calcified plaque interface there can be a local change in pH. The acidic functionalities can be the same or different from the calcium chelators. Chelators that can also provide an acidic environment can include, for example, ethylenediamine tetraacetic acid (EDTA) and molecules including other amino (imino) acid functional groups such as N-hydroxyethylenediaminetriacetic acid (HEDTA), diethylenetriaminepentaacetic acid (DTPA), and glycine. In some embodiments, a change in local pH (e.g., a decrease in local pH) can initiate a conversion of insoluble $CaCO_3$ into soluble calcium bicarbonate. Thus, a $Ca^{2+}$ cation can be easily captured by ion-exchange/chelating groups incorporated within the polymeric stent coating layer. In some embodiments, to enhance an acidic environment, acidic molecules such as ascorbic acid (vitamin C) can be incorporated into the hydrogel coating.

In some embodiments, the hydrogel layer can be positioned on the outside surface of the tubular expandable stent, around a circumference of the valve. The hydrogel layer can span the entire length of the tubular expandable stent, or span less than the entire length (e.g., up to about 90%, up to about 80%, up to about 70%, up to about 60%, up to about 50%, up to about 40%, up to about 30%, up to about 20%, or up to about 10% of the full length) of the tubular expandable stent, so long as the hydrogel layer covers a length around the circumference of the valve. The hydrogel layer can span the thickness of the valve, and when implanted, can fully cover a native valve that is now positioned between a body vessel and the heart valve system. In some embodiments, the hydrogel layer spans less than the full circumference of the tubular expandable stent, and gaps can exist between regions of the hydrogel layer. For example, the hydrogel layer can span up to about 80% (up to about 85%, up to about 90%, up to about 95%, up to about 99%) of the full circumference of the tubular expandable stent.

In some embodiments, the hydrogel is in the form of fibers, coatings, sheets, films, or viscous liquids, or a combination thereof. The fibers can have a sub-micron (e.g., less than one micron) width or diameter. In some embodiments, the fibers can have an average width or diameter from about five nm to about 500 nm. For example, the average width or diameter of the fibers can be greater than or equal to about five nm (e.g., greater than or equal to about 10 nm, greater than or equal to about 25 nm, greater than or equal to about 50 nm, greater than or equal to about 75 nm, greater than or equal to about 100 nm, greater than or equal to about 125 nm, greater than or equal to about 150 nm, greater than or equal to about 175 nm, greater than or equal to about 200 nm, greater than or equal to about 225 nm, greater than or equal to about 250 nm, greater than or equal to about 300 nm, greater than or equal to about 350 nm, greater than or equal to about 400 nm, or greater than or equal to about 450 nm); and/or less than or equal to about 500 nm (e.g., less than or equal to about 450 nm, less than or equal to about 400 nm, less than or equal to about 350 nm, less than or equal to about 300 nm, less than or equal to about 250 nm, less than or equal to about 225 nm, less than or equal to about 200 nm, less than or equal to about 175 nm, less than or equal to about 150 nm, less than or equal to about 125 nm, less than or equal to about 100 nm, less than or equal to about 75 nm, less than or equal to about 50 nm, less than or equal to about 25 nm, or less than or equal to about 10 nm). Fibers can provide a deformable open structure that can conform to a space around the valve, while acting at the same time as a network in which large debris can be captured. The open structure can allow access to plasma and endothelial progenitor cells, which can assist in covering the replaced native valve. In some embodiments, a fiber-network can form a barrier that captures large-particles and allows small particles (e.g., particles having an average maximum dimension of less than or equal to about 50 micrometers) to be removed by the bloodstream, where the open structure can allow the captured particles to be overgrown, encapsulated, and/or fixed by a cells.

The width or diameter of the hydrogel fibers can be substantially uniform along a length of a fiber, e.g., varying from about ±1 percent to about ±25 percent of the average width or diameter value over a fiber length. In some embodiments, a fiber is not perfectly circular in cross-section (e.g., oval, elliptical, regularly polygonal, or irregularly polygonal in cross section). The average width or diameter of the fiber having an irregular cross-section along a given length can refer to an average distance of any two orthogonal lines that both pass through the geometric center of the fiber cross-section and have end points on the perimeter of the fiber, or to the distance of any one such line.

In some embodiments, the fibers can have a length from about 10 Tm to about 10 cm. For example, the fiber length can be greater than or equal to about 10 Tm (e.g., greater than or equal to about 50 Tm, greater than or equal to about 100 Tm, greater than or equal to about 150 Tm, greater than or equal to about 500 Tm, greater than or equal to about 1 mm, greater than or equal to about 5 mm, greater than or equal to about 1 cm, greater than or equal to about 2 cm, greater than or equal to about 3 cm, greater than or equal to about 4 cm, greater than or equal to about 5 cm, greater than or equal to about 7 cm, greater than or equal to about 8 cm, or greater than or equal to about 9 cm); and/or less than or equal to about 10 cm (e.g., less than or equal to about 9 cm, less than or equal to about 8 cm, less than or equal to about 7 cm, less than or equal to about 5 cm, less than or equal to about 4 cm, less than or equal to about 3 cm, less than or equal to about 2 cm, less than or equal to about 1 cm, less than or equal to about 5 mm, less than or equal to about 1 mm, less than or equal to about 500 Tm, less than or equal to about 150 Tm, less than or equal to about 100 Tm, or less than or equal to about 50 Tm).

In some embodiments, when the hydrogel is in the form of a coating, a sheet, or a film, the hydrogel can have a thickness of from about 10 micrometers (e.g., from about 25 micrometers, from about 50 micrometers, from about 100 micrometers, from about 150 micrometers, from about 200 micrometers, from about 250 micrometers, from about 300 micrometers, from about 350 micrometers, from about 400 micrometers, or from about 450 micrometers) to about 500 micrometers (e.g., to about 450 micrometers, to about 400 micrometers, to about 350 micrometers, to about 300 micrometers, to about 250 micrometers, to about 200 micrometers, to about 150 micrometers, to about 100 micrometers, to about 50 micrometers, or to about 25 micrometers). For example, the hydrogel coating, sheet, or film can have a thickness greater than or equal to about 100 micrometers (e.g., greater than about 125 micrometers, greater than about 150 micrometers, greater than about 175 micrometers, greater than about 200 micrometers, or greater than or equal to about 225 micrometers) and/or less than or equal to about 250 micrometer (e.g., less than or equal to about 225 micrometers, less than or equal to about 200 micrometers, less than or equal to about 175 micrometers, less than or equal to about 150 micrometers, or less than or equal to about 125 micrometers). The coating, sheet, or film can be continuous or discontinuous, have perforations at regular or irregular intervals and of any size and/or shape, and/or can have variable thickness from one region to another. In some embodiments, the film, coating, or sheet can provide increased storage volume for chelators, compared to a fiber network. In some embodiments, a film can allow for dissolution and removal of calcium deposits by, for example, chelation of the calcium deposits.

In some embodiments, the hydrogel is in the form of a viscous liquid. The liquid can have a viscosity of from about 100 centipoise (e.g., from about 250 centipoise, from about 500 centipoise, from about 750 centipoise, from about 1000 centipoise, from about 1250 centipoise, from about 1500 centipoise, or from about 1750 centipoise) to about 2000 centipoise (e.g., to about 1750 centipoise, to about 1500 centipoise, to about 1250 centipoise, to about 1000 centipoise, to about 750 centipoise, to about 500 centipoise, or to about 250 centipoise). For example, the hydrogel viscous liquid can have a viscosity greater than or equal to about 500 centipoise (e.g., greater than or equal to about 600 centipoise, greater than or equal to about 700 centipoise, greater than or equal to about 800 centipoise, or greater than or equal to about 900 centipoise) and/or less than or equal to about 1000 centipoise (e.g., less than or equal to about 900 centipoise, less than or equal to about 800 centipoise, less than or equal to about 700 centipoise, or less than or equal to about 600 centipoise). In some embodiments, a larger volume of a liquid can be delivered compared to a hydrogel film, coating, or sheet, or a fiber system. A liquid can provide greater adaptability (e.g., can conform to) to open volumes around the implanted valve.

In some embodiments, when a liquid contains monomers or oligomers, the monomers or oligomers can have reactive end groups that can be further polymerized (e.g., crosslinked) by physical or chemical crosslinking. Examples of reactive end groups can include, for example, hydroxyl, allyl, amine, isocyanate, cyano, carboxylate, anhydride, halide, silane, thiol, azide, activated ester, acrylate, and/or aldehyde. For example, chemical crosslinking can occur by photopolymerization. In some embodiments, physical crosslinking can occur by stereocomplexation of two or more types of molecules. For example, stereocomplexed hydrogels can be obtained by mixing aqueous solutions of molecules grafted with L-lactic acid oligomers and D-lactic acid oligomers. In some embodiments, without wishing to be bound by theory, it is believed that gelation can occur due to stereocomplex formation of oligomers of opposite chirality (e.g., D- and L-lactic acids). In some embodiments, stereocomplexation hydrogels can occur with water-soluble poly (L-lactide) and poly(D-lactide) copolymers or dextran-lactide hydrogels. Examples of stereocomplexation is described, for example, in Jun et al., Macromolecular Research, 16(8), 704-710 (2008), herein incorporated by reference. In some embodiments, a liquid can contain a gel that is fluid at lower temperatures (e.g., below 30° C.) and that gelates at higher temperatures (e.g., from 30 to 37° C.). The liquid can, for example, contain a temperature-responsive polymer such as polyacrylamide, polymethacrylamide and/or poly(N-isopropylacrylamide).

The hydrogel can include natural and/or synthetic polymers, such as oligo(amidoamine/β-amino ester), methyl cellulose, collagen, gelatin, chitosan, hyaluronic acid, chondroitin sulfate, alginate, agar, agarose, fibrin, polyethylene glycol, polyethylene oxide, polyvinyl alcohol, poly(propylene fumarate), oligo(polyethylene glycol) fumarate, poly(N-isopropylacrylamide), polypropylene oxide, poly(aldehyde guluronate), polylactic acid, polyglycolic acid, poly(lactic-co-glycolic) acid, polyanhydride (e.g., poly(sebacic acid-co-1,3-bis(p-carboxyphenoxy) propane) (P(CPP-SA)), combinations thereof, and/or copolymers thereof. Examples of polyanhydrides are described, for example, in Kumar et al., Advanced Drug Delivery Reviews 54, 889-910 (2002).

In some embodiments, the hydrogel can include frangible capsules (e.g., microcapsules) that can rupture upon application of a critical pressure. The microcapsules can enclose one or more therapeutic agents, one or more acidifying agents, and/or one or more calcium-chelating agents. In some embodiments, the capsules can rupture upon delivery and expansion of a vascular valve system to deliver encapsulated agents. The microcapsules can have a multilayer polyelectrolyte shell. In some embodiments, the capsules are ceramic capsules. Frangible capsules, critical pressures, and methods of making and delivering frangible capsules are described, for example, in U.S. Pat. No. 7,364,585 and U.S. Application Ser. No. 61/421,054, filed Dec. 8, 2010, each herein incorporated by reference in its entirety.

Without wishing to be bound by theory, it is believed that ion exchange processes using acidic or Na cation exchangers can remove calcium from a variety of media. For example, a number of ion-exchange or chelating functional groups can selectively bind calcium and be used for calcium removal. Functional groups such as amino diacetic acid and —$CH_2$—NH—$CH_2$—$PO_3Na$ are used in commercially microporous resin products (e.g., Ionac SR-5 and Amberlite IRC 747) for calcium extraction/removal, respectively. In some embodiments, ethylenediamine tetraacetic acid (EDTA) and other amino acid derivatives (e.g., N-hydroxyethylenediaminetriacetic acid (HEDTA), diethylenetriaminepentaacetic acid (DTPA) and glycine) can be efficient chelating agents for calcium. Other chemical compounds that can act as calcium binders include, for example, citric acids and phosphonates (e.g., HPDP (1-hydroxo-3-aminopropane-1,1-diphosphonate), or HEDP (hydroxyethyl-1,1-diphosphonate)).

In some embodiments, the calcium-chelating agent includes ethylenediamine tetraacetic acid, phosphonates, 1,2-bis(2-aminophenoxy)ethane-N,N,N',N'-tetraacetic acid, ethylene glycol-bis(2-aminoethylether)-N,N,N',N'-tetraacetic acid, trans-1,2-cyclohexanediaminetetraacetic acid, N-hydroxyethylenediaminetriacetic acid (HEDTA), diethylenetriaminepentaacetic acid (DTPA), glycine, 2,2'-bipyridyl, dimercaptopropanol, ionophores, nitrilotriacetic acid, NTA ortho-phenanthroline, gramicidin, monensin, valinomycin, salicylic acid, triethanolamine (TEA), polysaccharides, organic acids with at least two coordination groups (e.g., citric acid, or citric acid together with acetic acid), lipids, steroids, amino acids, peptides, phosphates, nucleotides, tetrapyrrols, ferrioxamines, and/or phenolics. The calcium-chelating agent can be used singly or in combination, and/or can be delivered to the area surrounding and including a calcified valve. The calcium-chelating agent can be in the form of microparticles, nanoparticles, or nanocrystals; or microspheres or nanospheres containing or bound to one or more chelating agents. The microspheres or nanospheres can include one or more biocompatible materials such as polylactic acid, polyamide esters, polyvinyl esters, polyvinyl alcohol, polyanhydrides, natural biodegradable polymers, polysaccharides, and derivatives thereof. The calcium-chelating agent can be covalently bound, ionically bound, and/or physically adsorbed to the hydrogel. Examples of covalent bonds include, for example, enzyme and hydrolytically cleavable bonds such as ester, amide, anhydride, and carbamide linkages, and/or acid-cleavable groups such as —OC(O)—, —C(O)O—, or —C=NN—. In some embodiments, a calcium-chelating agent is dissolved in a hydrogel.

In some embodiments, the hydrogel includes from about one percent (e.g., from about two percent, from about three percent, from about four percent, from about five percent, from about six percent, from about seven percent, from about eight percent, or from about nine percent) to about 10 percent (e.g., to about nine percent, to about eight percent, to about seven percent, to about six percent, to about five percent, to about four percent, to about three percent, or to about two percent) by weight of the calcium-chelating agent.

In some embodiments, the acidifying agent includes citric acid, ascorbic acid, acetic acid, and/or lactic acid. The acidifying agent can be covalently bound, ionically bound, and/or physically adsorbed to the hydrogel. The acidifying agent can be in the form of microparticles, nanoparticles, or nanocrystals; or microspheres or nanospheres containing or bound to one or more acidifying agents. In some embodiments, the hydrogel includes from about 0.5% percent (e.g., from about one percent, from about two percent, from about five percent, from about seven percent, from about 10 percent, from about 15 percent, or from about 17 percent) to about 20% (e.g., to about 17 percent, to about 15 percent, to about 10 percent, to about seven percent, to about five percent, to about two percent, or to about one percent) of the acidifying agent.

Figure 3:
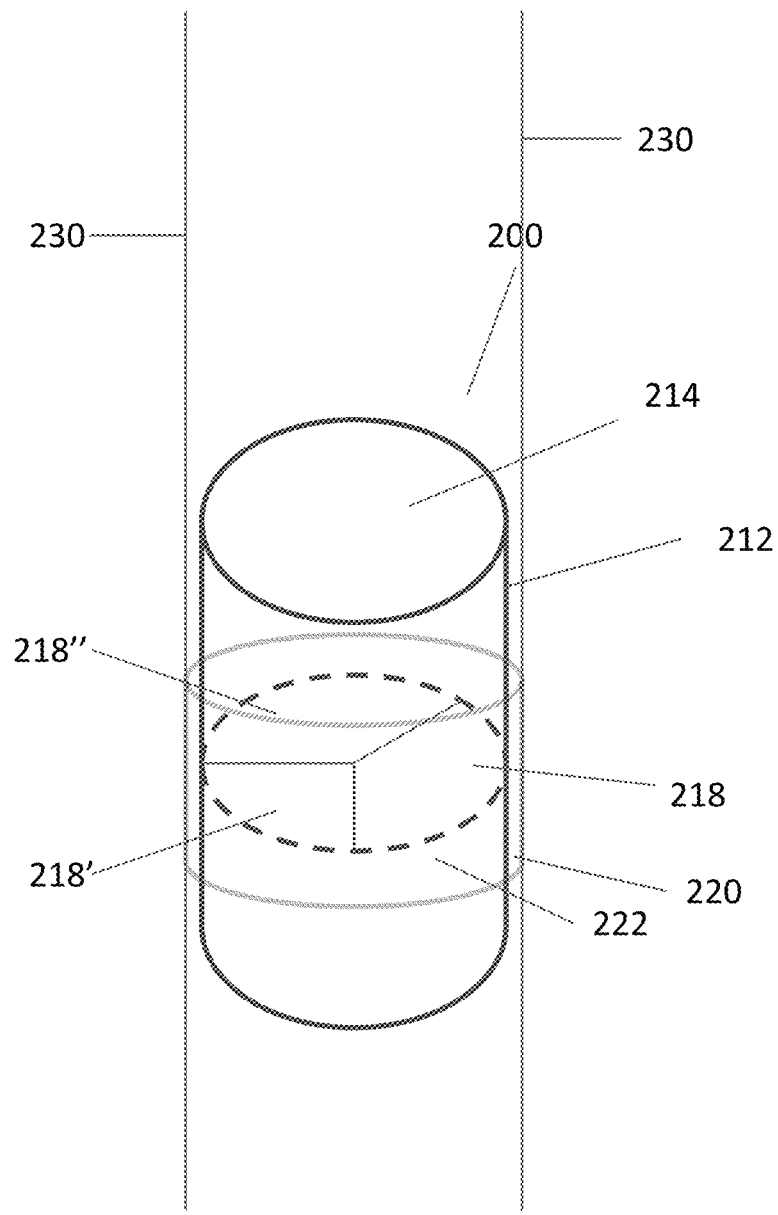
FIG. 3 shows an embodiment of a vascular valve system.

Referring to FIG. 3, in some embodiments, instead of coating a heart valve system 200 with a hydrogel including calcium chelators and/or acidifying agents, a hydrogel composition 222 can be injected into a housing 220, between the heart valve system and vessel wall 230. The heart valve system 200 can include a prosthetic valve having a plurality of leaflets 218, 218', and 218", within a lumen 214 of an expandable stent 212. The hydrogel composition can be biodegradable. In some embodiments, the hydrogel composition includes, for example, oligo(amidoamine/β-amino ester), gelatins, collagen, chitosan, hyaluronic acid, chondroitin sulfate, alginate, agar, agarose, fibrin, polyethylene glycol, polyethylene oxide, polyvinyl alcohol, poly(propylene fumarate), oligo(polyethylene glycol) fumarate, poly(N-isopropylacrylamide), polypropylene oxide, poly(aldehyde guluronate), polylactic acid, polyglycolic acid, poly(lactic-co-glycolic) acid, and/or polyanhydride. Examples of injectable hydrogels are described, for example, in Tan et al., Materials 2010, 3, 1746-1767, herein incorporated by reference. The housing can be permeable, such that hydrogel compositions, calcium particles, and bodily fluids can flow into and chelated molecules can flow out of the housing. In some embodiments, the housing is dissolvable or absorbable.

In some embodiments, the housing is porous. The pores can allow a reasonable quick flow or interaction with the environment. In some embodiments, a high density of pores can allow for quick flow or interaction with the environment. For example, the housing can include pores (e.g., laser ablated pores) having an average diameter of from about 10 micrometers (e.g., from about 25 micrometers, from about 50 micrometers, or from about 75 micrometers) to about 100 micrometers (e.g., to about 75 micrometers, to about 50 micrometers, or to about 25 micrometers). As used herein, a density of pores on a housing is an area of porous area over a total surface area of a housing. In some embodiments, the pore density can be from about five percent (e.g., from about 10 percent, from about 15 percent, from about 20 percent, from about 25 percent, from about 30 percent, from about 35 percent, from about 40 percent, or from about 45 percent) to about 50 percent (e.g., to about 45 percent, to about 40 percent, to about 35 percent, to about 30 percent, to about 25 percent, to about 20 percent, to about 15 percent, or to about 10 percent).

Figure 4:
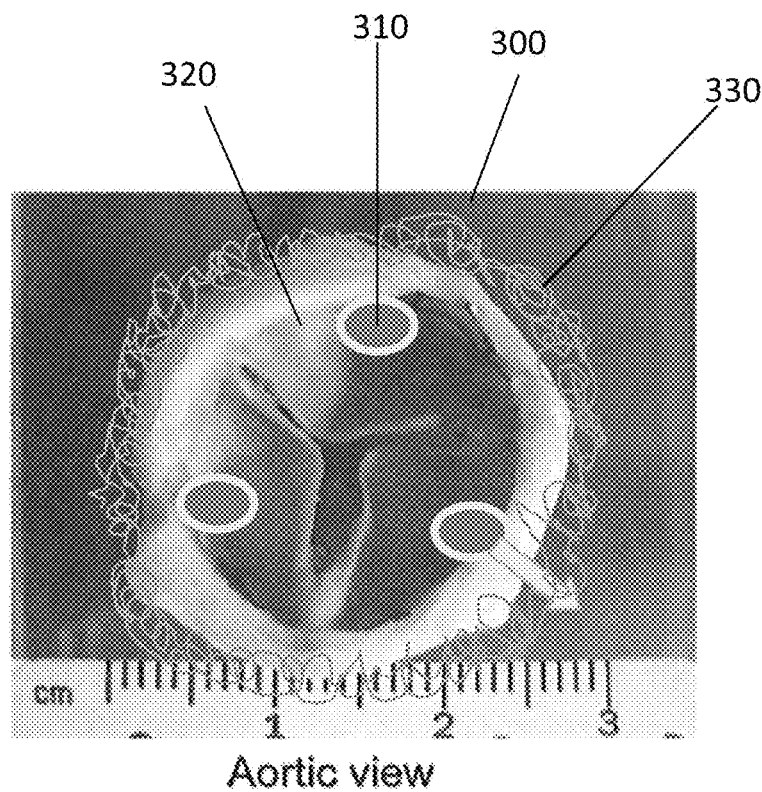
FIG. 4 shows an embodiment of a vascular valve system.

The housing can be disposed within or on the outside of a heart valve system. For example, in some embodiments, a housing can be disposed on an inside wall of a heart valve system, and a fiber spun network can be disposed on an outside surface of the heart valve system. Referring to FIG. 4, a heart valve system 300 can have housing 310 in the form of pockets including chelators and/or therapeutic agent on replacement heart valves 320. The valves can function while minimally mechanically affected by the pockets. As shown in FIG. 4, the heart valve system can have a fiber network 330 on the exterior surface of the system, which can, for example, capture larger calcified deposits or plaques. Housings 310 can be filled after the heart valve system has been implanted. The housings on the inner side of the valve can minimize interference with a blood stream going to the aortic arteries. In some embodiments, the housing can include a double layer of polymer, for example, a polymeric first layer (e.g., polyurethane, PLGA) covering on a valve housing second layer. In some embodiments, the housing can include thin guidewires that are inserted into the housing (pockets) and through the delivery catheter, such that an injection catheter can be guided over these wires into the empty pockets and inject a hydrogel composition. The guidewires can serve as an assist-element of the valve system, and can be removed after valve implantation. After filling the housing, both wire and catheter can be pulled out of the housing.

Figures 5A, 5B:
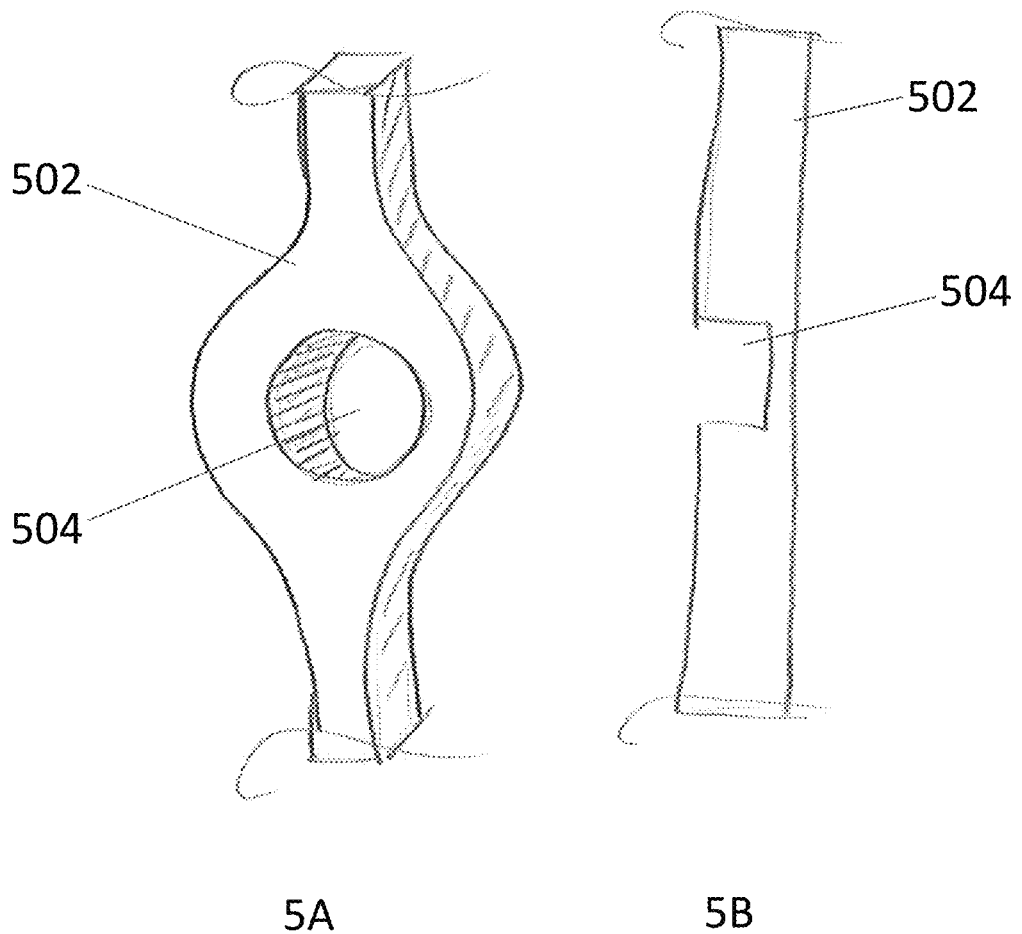
FIGS. 5A-5B shows an embodiment of a vascular valve system.

In some embodiments, a housing is in the form of a cavity (e.g., partial cavity or through cavity). The cavity can be created by ablating cavities (e.g., partial cavities and/or through cavities) in the stent framework of the valve system. These cavities can be located on the outward facing surfaces and/or the sidewalls. Referring to FIGS. 5A and 5B, a stent strut 502's width can be made wider at the location of each cavity 504. FIG. 5B is a cross-sectional side view of a stent strut 502 with the partial cavity 504. In some embodiments, the housing can be positioned on the outside surface of the tubular expandable stent, around a circumference of the valve. The housing can span the entire length of the tubular expandable stent, or can span less than the entire length (e.g., less than or about 90%, less than or about 80%, less than or about 70%, less than or about 60%, less than or about 50%, less than or about 40%, less than or about 30%, less than or about 20%, or less than or about 10% of the full length) of the tubular expandable stent, so long as the housing covers a length around the circumference of the valve. The housing can span the thickness of the valve, and when implanted, can fully cover a native valve that is now positioned between a body vessel and the heart valve system.

In use, the vascular valve system can be implanted into a vessel via a TAVI procedure. When expanded and implanted into a vessel, a hydrogel coating can be pressed against a native calcified valve, or a hydrogel composition can be injected into a housing surrounding the vascular valve system, which presses against a native calcified valve. Loosened calcium deposits can be captured by the hydrogel, and the calcium-chelating agent can bind to calcium in the calcium deposits. The calcium-calcium chelating agent complex can leach out of the hydrogel and be removed from the calcified valve with bodily fluids (e.g., blood). In some embodiments, when the calcium-chelating agent is covalently bound to a hydrogel, the covalent bond can be cleaved under physiological conditions, and the calcium-calcium chelating agent can be released from the hydrogel and removed from the calcified valve with bodily fluids.

In some embodiments, micro-magnets can be embedded near the bottom of the vascular valve system, within and/or against a polymer skirt. For example, the micro-magnets can be embedded on the inner facing surface and/or outer surface. The micro-magnets can help localize the delivery of therapeutic and/or calcium-chelating agent-encapsulating magnetic particles. For example, magnetic microspheres can be formed of a hydrogel (see, e.g., supra) in which a magnetizable material, such as magnetite, and a drug are embedded. The microspheres can be injected into a space between the polymer inner skirt and a native vessel (e.g., blood vessel). In a magnetic system, the drug and/or calcium chelating agent can be re-loaded from time to time, or more of the drug and/or calcium chelating agent can be administered at an area having the most calcifications. In some embodiments, a sequence of the same or different drugs and chelators can be administered at different time points.

In some embodiments, a hydrogel coating is applied by spray coating a substrate (e.g., a vascular valve system) with a solution including polymers (e.g., hydrogel-forming polymers), calcium chelators, acidifying agents, and solvents. In some embodiments, the solution can include one or more therapeutic agents. The solvents can include tetrahydrofuran, methanol, acetone, chloroform, other volatile solvents, and/or water. A vascular valve system can be coated either in its expanded state, contracted state, or semi-contracted state.

In some embodiments, the hydrogel coating is applied by electro-spraying a substrate (e.g., a vascular valve system) with a solution including polymers (e.g., hydrogel-forming polymers), calcium chelators, acidifying agents, and solvents.

Electrospraying can create a fiber network of hydrogel. In particular, by controlling the voltage, flow-rate, concentration of polymers in the spray fluid, the viscosity of the spray fluid, and the distance of the nozzle from the surface of the substrate, the width or diameter of the fibers formed during the spinning process can be controlled. Environmental factors, such as temperature, pressure, solvent vapor pressure, can also determine the diameter of the fibers.

In some embodiments, the hydrogel coating can include one or more polymers, which can, for example, include hydrogel-forming polymers and polymers that do not form hydrogels. Examples of polymers include without limitation oligo(amidoamine/β-amino ester), methyl cellulose, collagen, gelatin, chitosan, hyaluronic acid, chondroitin sulfate, alginate, agar, agarose, fibrin, albumin, polyethylene glycol, polyethylene oxide, polyvinyl alcohol, poly(propylene fumarate), oligo(polyethylene glycol) fumarate, poly(N-isopropylacrylamide), polypropylene oxide, poly(aldehyde guluronate), polylactic acid, polyglycolic acid, poly(lactic-co-glycolic) acid, polyanhydride (e.g., poly(sebacic acid-co-1,3-bis(p-carboxyphenoxy) propane) (P(CPP-SA)), combinations thereof, and/or copolymers thereof. The hydrogel composition can be crosslinkable, for example, the hydrogel composition can include polymers such as polyethylene glycol diacrylate (PEGDA) and poly(ethylene glycol) dimethacrylate (PEGDMA). In some embodiments, crosslinkable hydrogels can be crosslinked ex vivo or in situ. Examples of crosslinking include, for example, reversible or irreversible chemical and/or physical crosslinking. In some embodiments, biodegradable gels can be made by mixing polyanions and polycations, for example dextran or heparin (anions) with either poly(vinylbenzyltrimethyl)-ammonium hydroxide or chitosan. In certain embodiments, an in-situ crosslinking reaction can occur without heat or radiation. For example, systems that can be gelated by stereo-complexation like PEG-(PLA) or PEG-PLA-PEG are suitable. In some embodiments, the polymers can degrade and be removed from the treatment site within a defined period of time (e.g., for a time period of one day to one week, for a month, for a year, or more). In some embodiments, after release of the calcium-chelating agent is complete, the hydrogel degrades and disperses from the treatment site.

In some embodiments, a combination of coating methods can be used to deposit various hydrogels, polymers, and/or therapeutic agents, in addition to the deposition methods described above. For example, methods such as conventional nozzle or ultrasonic nozzle spraying, dipping, rolling, electrostatic deposition, and a batch process such as air suspension, pancoating or ultrasonic mist spraying can be used to coat the vascular valve system.

In some embodiments, it may be desirable to roughen a surface of interest before performing depositions described herein. For example, a surface may be roughened to provide a series of nooks or invaginations on/within the surface. Any surface may be roughened, e.g., a metallic, polymeric or ceramic surface. Surfaces can be roughened using any technique known in the art. Particularly useful methods for roughening surfaces, such as the surfaces of a stent, are described, e.g., in U.S. Ser. No. 12/205,004, which is hereby incorporated by reference.

Further, as will be appreciated by skilled practitioners, coatings described herein can be deposited on an entire surface of a device or onto only part of a surface. This can be accomplished using masks to shield the portions on which coatings are not to be deposited. Further, with regard to vascular valve systems, it may be desirable to deposit only on the abluminal surface of the vascular valve system. This construction may be accomplished by, e.g. coating the vascular valve system before forming the fenestrations. In other embodiments, it may be desirable to deposit only on abluminal and cutface surfaces of the vascular valve system. This construction may be accomplished by, e.g., depositing on a vascular valve system containing a mandrel, which shields the luminal surfaces.

The hydrogels can include a therapeutic agent, such as paclitaxel, everolimus, rapamycin, biolimus, zotarolimus, tacrolimus, sirolimus, tacrolimus, heparin, diclofenac, and/or aspirin. The terms "therapeutic agent", "pharmaceutically active agent", "pharmaceutically active material", "pharmaceutically active ingredient", "drug" and other related terms may be used interchangeably herein and include, but are not limited to, small organic molecules, peptides, oligopeptides, proteins, nucleic acids, oligonucleotides, genetic therapeutic agents, non-genetic therapeutic agents, vectors for delivery of genetic therapeutic agents, cells, and therapeutic agents identified as candidates for vascular treatment regimens, for example, as agents that reduce or inhibit restenosis. By small organic molecule is meant an organic molecule having 50 or fewer carbon atoms, and fewer than 100 non-hydrogen atoms in total. The therapeutic agent can be amorphous.

Exemplary non-genetic therapeutic agents include anti-thrombogenic agents such as heparin, heparin derivatives, prostaglandin (including micellar prostaglandin E1), urokinase, and PPack (dextrophenylalanine proline arginine chloromethylketone); anti-proliferative agents such as enoxaparin and angiopeptin, monoclonal antibodies capable of blocking smooth muscle cell proliferation, hirudin, and acetylsalicylic acid; anti-inflammatory agents such as dexamethasone, rosiglitazone, prednisolone, corticosterone, budesonide, estrogen, estrodiol, sulfasalazine, acetylsalicylic acid, mycophenolic acid, and mesalamine; anti-neoplastic/anti-proliferative/anti-mitotic agents such as paclitaxel, epothilone, cladribine, 5-fluorouracil, methotrexate, doxorubicin, daunorubicin, cyclosporine, cisplatin, vinblastine, vincristine, epothilones, endostatin, trapidil, halofuginone, and angiostatin; anti-cancer agents such as antisense inhibitors of c-myc oncogene; antimicrobial agents such as triclosan, cephalosporins, aminoglycosides, nitrofurantoin, silver ions, compounds, or salts; biofilm synthesis inhibitors such as non-steroidal anti-inflammatory agents; antibiotics such as gentamycin, rifampin, minocyclin, and ciprofloxacin; antibodies including chimeric antibodies and antibody fragments; anesthetic agents such as lidocaine, bupivacaine, and ropivacaine; nitric oxide; nitric oxide (NO) donors such as linsidomine, molsidomine, L-arginine, NO-carbohydrate adducts, polymeric or oligomeric NO adducts; anti-coagulants such as D-Phe-Pro-Arg chloromethyl ketone, an RGD peptide-containing compound, heparin, anti-thrombin compounds, platelet receptor antagonists, anti-thrombin antibodies, anti-platelet receptor antibodies, enoxaparin, hirudin, warfarin sodium, Dicumarol, aspirin, prostaglandin inhibitors, platelet aggregation inhibitors such as cilostazol and tick antiplatelet factors; vascular cell growth promotors such as growth factors, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vascoactive mechanisms; inhibitors of heat shock proteins such as geldanamycin; angiotensin converting enzyme (ACE) inhibitors; beta-blockers; βAR kinase (βARK) inhibitors; phospholamban inhibitors; protein bound particle drugs such as ABRAXANE™; structural protein (e.g., collagen) cross-link breakers such as alagebrium (ALT-711); and/or any combinations and prodrugs of the above.

Exemplary biomolecules include peptides, polypeptides and proteins; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors; and anti-restenosis agents. Nucleic acids may be incorporated into delivery systems such as, for example, vectors (including viral vectors), plasmids or liposomes.

Non-limiting examples of proteins include serca-2 protein, monocyte chemoattractant proteins (MCP-1) and bone morphogenic proteins ("BMPs"), such as, for example, BMP-2, BMP-3, BMP-4, BMP-5, BMP-6 (VGR-1), BMP-7 (OP-1), BMP-8, BMP-9, BMP-10, BMP-11, BMP-12, BMP-13, BMP-14, and BMP-15. Preferred BMPs are any of BMP-2, BMP-3, BMP-4, BMP-5, BMP-6, and BMP-7. These BMPs can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNAs encoding them. Non-limiting examples of genes include survival genes that protect against cell death, such as antiapoptotic Bcl-2 family factors and Akt kinase; serca 2 gene; and combinations thereof. Non-limiting examples of angiogenic factors include acidic and basic fibroblast growth factors, vascular endothelial growth factor, epidermal growth factor, transforming growth factors α and β, platelet-derived endothelial growth factor, platelet-derived growth factor, tumor necrosis factor a, hepatocyte growth factor, and insulin-like growth factor. A non-limiting example of a cell cycle inhibitor is a cathepsin D (CD) inhibitor. Non-limiting examples of anti-restenosis agents include p15, p16, p18, p19, p21, p27, p53, p57, Rb, nFkB and E2F decoys, thymidine kinase and combinations thereof and other agents useful for interfering with cell proliferation.

Exemplary small molecules include hormones, nucleotides, amino acids, sugars, and lipids and compounds having a molecular weight of less than 100 kD.

Any vascular valve system described herein can be dyed or rendered radiopaque by addition of, e.g., radiopaque materials such as barium sulfate, platinum or gold, or by coating with a radiopaque material. The vascular valve system can include (e.g., be manufactured from) metallic materials, such as stainless steel (e.g., 316L, BioDur® 108 (UNS S29108), and 304L stainless steel, and an alloy including stainless steel and 5-60% by weight of one or more radiopaque elements (e.g., Pt, Jr, Au, W) (PERSS®) as described in US-2003-0018380-A1, US-2002-0144757-A1, and US-2003-0077200-A1), Nitinol (a nickel-titanium alloy), cobalt alloys such as Elgiloy, L605 alloys, MP35N, titanium, titanium alloys (e.g., Ti-6Al-4V, Ti-50Ta, Ti-10Ir), platinum, platinum alloys, niobium, niobium alloys (e.g., Nb-1Zr) Co-28Cr-6Mo, tantalum, and tantalum alloys. Other examples of materials are described in commonly assigned U.S. application Ser. No. 10/672,891, filed Sep. 26, 2003; and U.S. application Ser. No. 11/035,316, filed Jan. 3, 2005. Other materials include elastic biocompatible metal such as a superelastic or pseudo-elastic metal alloy, as described, for example, in Schetsky, L. McDonald, "Shape Memory Alloys", Encyclopedia of Chemical Technology (3rd ed.), John Wiley & Sons, 1982, vol. 20. pp. 726-736; and commonly assigned U.S. application Ser. No. 10/346,487, filed Jan. 17, 2003.

EXAMPLES

Example 1

Figure 6A:
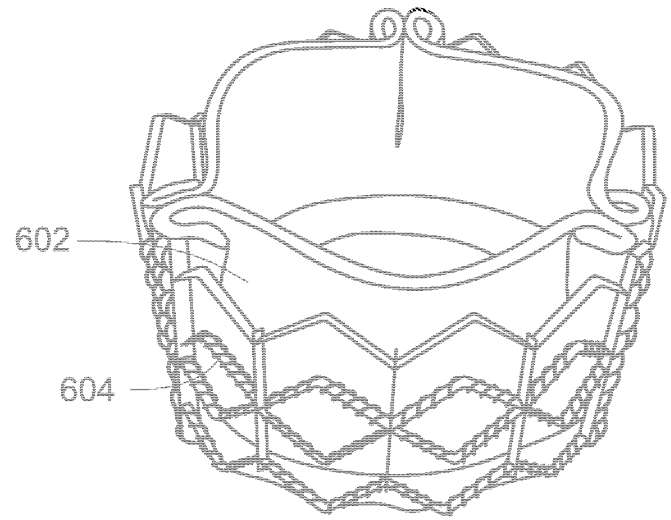
FIGS. 6A-6B shows an embodiment of a vascular valve system.
Figure 6B:
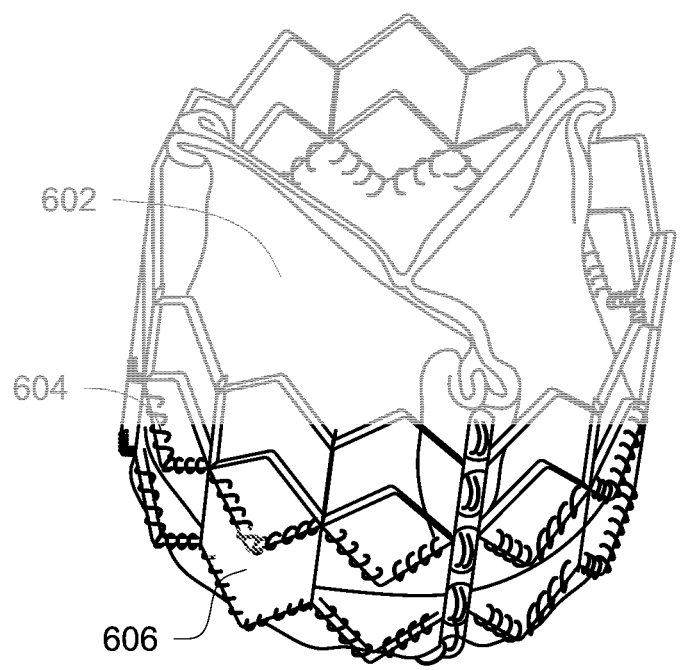

Heart Valve with Internal Housing of Polyethylene Terephthalate and an External Electrospun Fiber Network of PLGA A finished heart valve with a PET outer skirt is first being provided with a series of empty depots (i.e., pockets, or housings). Referring to FIG. 6A, a balloon expandable heart valve with a polyethylene terephthalate (PET) inner skirt 602, mounted by stitches 604 on the inside of a stent frame, is used as a starting point. A Ultra-thin Polyester (Mylar®) 0.00014" (3.6 µm) PET foil (SPI Supplies West Chester, Pa.) is cut into a 15 mm strip by 200 mm and placed flat on a stainless steel surface. In some embodiments, the length of the ultra-thin polyester is not important, as long as it is longer than the polymer skirt film. The polyester is glued with ethyl cyanoacrylate to the skirt and cut to equal length as the skirt before being sewn to the stent, and the end (2 cm) of a stainless steel wire (0.014" diameter) is inserted in between the skirt and foil. The film is provided with 20 micrometer diameter holes at a ratio of 10% of the total surface area using a mask in combination with a KrF laser (248 nm) (Lambda Physik EMG201, 30 ns), set a laser fluence of 35 mJ/cm². The perforated film 606 is glued circumferentially to the skirt before mounting the skirt to the stent. In other words, the laser ablated film is glued as stripes on top and bottom to the PET skirt, and then sewn as shown in FIG. 6B on the inside of the stent.

An electrospun layer is then created on the external surface of the heart valve. A 100 ml solution is prepared at room temperature, the solution includes 3:1 THF:DMF and 3 g/ml PLGA (Sigma Aldrich). The solution is stirred for 24 hours. The heart valve is placed on a Teflon turn table which allows rotation of the valve at a speed of 12 RPM, rotating the table repeatedly for 5 clockwise rotations and 5 counterclockwise rotations to avoid disconnecting of the ground wire. The housing of the heart valve is connected by a vertical wire to ground. A 60 mL syringe is filled with the solution and a Teflon tubing is connected between syringe and a 35 gauge needle. The point of the needle is placed 12 cm from the housing. The syringe (60 ml) is placed in a syringe pump (NE-1000 Programmable Single Syringe Pump: New Era Pump Systems Inc.). The syringe pump is run at 2 ml/hr. The needle is connected to a high voltage supply (CZE1000R, Spellman United Kingdom, West Sussex). The high voltage supply is set at 12 kV and the process is run for approx. 10 minutes. The solution is sprayed over the bottom 10 mm of the housing (masking the area where there is no skirt) and forms a network of about 4 mm thick at a volume density of about 10%.

The whole assembly is crimped onto a 25 mm balloon and expanded at the position of the original native heart valve. After removing the delivery system of the valve, a Fr 3 catheter can be inserted over the wire going into the depots. A thermo-sensitive hydrogel solution was made by slowly mixing 35% by weight Pluronic F-127 (Sigma-Aldrich) in 5 degrees Celsius water and adding 2 mg/ml L-Ascorbic acid (Sigma-Aldrich). The solution was maintained at 5 degrees Celsius before injecting 1.6 ml into the depots of placed heart valve. The delivery tube was pulled out after 60 seconds.

Example 2

Figure 7:
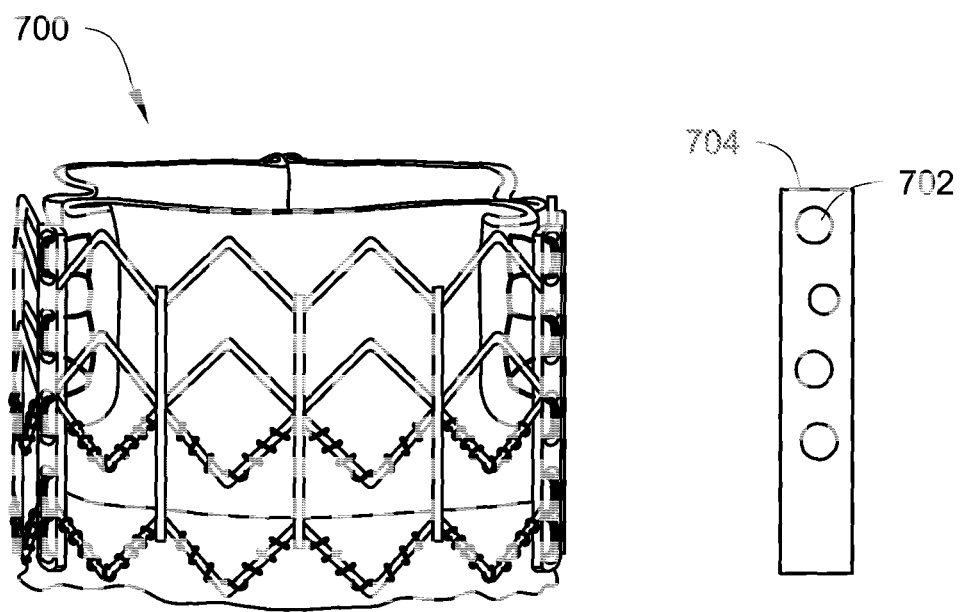
FIG. 7 shows an embodiment of a vascular valve system.

Heart Valve with Ablated Cavities in a Stent Framework, Functioning as Reservoirs for Calcium Chelators Referring to FIG. 7, a finished stainless steel heart valve stent frame 700 is being provided with a series of empty cavities 702 on stent strut 704. The metal housing is provided with 50 micrometer diameter, 100 micrometer deep cavities using an excimer laser (351 nm) (Coherent Xantos XS-500-351 nm, 16 ns pulse width), set at a laser fluence of 100 J/cm², utilizing sequences of 300 pulses). The cavities are located at the outside of the housing, centered along the middle axis of the struts with a distance between the holes of 300 micrometer. Providing 20 cavities between each connection point.

A 100 ml solution is prepared at room temperature, the solution includes 3:1 THF:DMF, 3 g/ml PLGA (Sigma Aldrich), and 5% by weight of Everolimus. The solution is stirred for 24 hours and inkjet printed in the cavities using a "Autodrop" system from Microdrop (Microdrop Technologies GmbH, Muehlenweg 143, D-22844 Norderstedt Germany), after which further assembly is carried out.

Example 3

Heart Valve System Including Embedded Magnetic Microspheres

Figure 8:
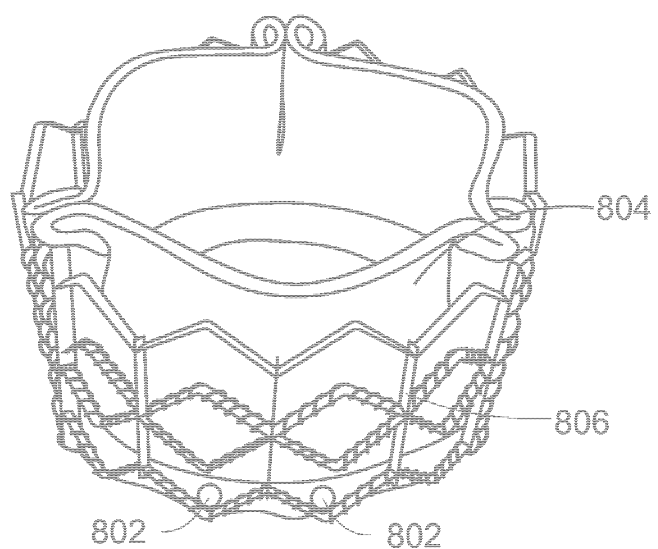
FIG. 8 shows an embodiment of a vascular valve system.
Like reference symbols in the various drawings indicate like elements.

Six Neodynium micro magnets are purchased from BJA magnetics (BJA Magnetics, Leominster, Mass.), in the form of discs having a 0.040" outer diameter, a 0.01" inner diameter, and 0.006" thickness. The magnets are provided by the manufacturer with a parylene coating and are glued to a polyethylene terephthalate skirt of a balloon expandable valve system, using a medical grade MP-21HP two-component primer and instant adhesive from Loctite (Loctite, Nieuwegein, Netherlands). The location (and small size) of two of the six micromagnets 802 is shown in FIG. 8. The PET skirt 804, located within a stent frame 806, is perforated in the area surrounding the magnets with 10 times 0.005" diameter holes using an ablation laser (e.g., an excimer 356 nm laser). The valve is crimped on a balloon and implanted per normal procedure.

A Renegade Hi-Flow Fr 3. Microcatheter is provided at the tip with a Parylene coated iron markerband, which is attached to the tip of the microcatheter using a PET shrinktube (Advanced polymers, Salem, N.H.), 2 mm located from the distal end. The microcatheter is inserted over a 0.14" Guide Wire (Synchro2, Boston Scientific) to be near the location of the micromagnets. The magnetic attraction between the micromagnets and the iron markerbands is used to keep the tip of the micro-catheter located near the magnets.

Magnetic biodegradable PLGA particles loaded with Everolimus as made per recipe as described by Asmatulu, R. et al., Drug-Carrying Magnetic Nanocomposite Particles for Potential Drug Delivery Systems, Journal of Nanotechnology, Volume 2009 (2009), Article ID 238536, herein incorporated by reference in its entirety, were produced and injected (dissolved in saline) via the micro-catheter. The magnetic particles can diffuse out of the perforated holes in the PET skirt to the area between the skirt and the native blood vessel. The magnetic particles can remain in the area between the skirt and the native blood vessel, near the proximity of the micro magnets.

All non-patent literature publications, patent applications, patent application publications, and patents, referred to in the instant application are incorporated herein by reference in their entirety.

A number of embodiments of the invention have been described. Nevertheless, it will be understood that various modifications may be made without departing from the spirit and scope of the invention. Accordingly, other embodiments are within the scope of the following claims.

The invention claimed is:

1. A vascular valve system comprising:
    an expandable stent comprising an outer surface and a lumen;
    a valve comprising a plurality of leaflets, wherein the valve is disposed within the lumen of the expandable stent; and
    a material layer adjacent to at least a portion of the valve and disposed on the outer surface of the expandable stent, the material layer comprising a hydrogel, a calcium-chelating agent, and an acidifying agent;
    wherein the hydrogel comprises a network of electrospun fibers; and
    wherein the acidifying agent is selected from the group consisting of ascorbic acid, acetic acid, lactic acid, and any combination thereof; and
    wherein the acidifying agent is present in the hydrogel at from 0.5 percent to 15 percent by weight; and
    wherein the acidifying agent is effective to decrease a local pH to initiate a conversion of insoluble calcium carbonate ($CaCO_3$) into soluble calcium bicarbonate.

2. The vascular valve system of claim 1, wherein the valve comprises at least one of a tissue or a polymeric material.

3. The vascular valve system of claim 2, wherein the tissue comprising porcine pericardium.

4. The vascular valve system of claim 1, wherein the valve is attached to the expandable stent with a plurality of sutures.

5. The vascular valve system of claim 1, wherein the material layer is disposed around a circumference of the valve.

6. The vascular valve system of claim 1, wherein the material layer is disposed on a portion of the valve.

7. The vascular valve system of claim 1, wherein the hydrogel is selected from the group consisting of oligo (amidoamine/(β-amino ester), gelatin, methyl cellulose, collagen, chitosan, hyaluronic acid, chondroitin sulfate, alginate, agar, agarose, fibrin, polyethylene glycol, polyethylene oxide, polyvinyl alcohol, poly(propylene fumarate), oligo(polyethylene glycol) fumarate, poly(N-isopropylacrylamide), polypropylene oxide, poly(aldehyde guluronate), polylactic acid, polyglycolic acid, poly(lactic-co-glycolic) acid, polyanhydride, combinations thereof, and copolymers thereof.

8. The vascular valve system of claim 1, wherein the calcium-chelating agent is selected from the group consisting of ethylene diamine tetraacetic acid, phosphonates, 1,2-bis(2-aminophenoxy)ethane-N,N,N',N'-tetraacetic acid, ethylene glycol-bis(2-aminoethylether)-N,N,N',N'-tetraacetic acid, trans-1,2-cyclohexanediaminetetraacetic acid, N-hydroxyethylenediaminetriacetic acid, diethylenetriaminepentaacetic acid, and glycine.

9. The vascular valve system of claim 1, wherein the calcium-chelating agent is covalently bound to the hydrogel.

10. The vascular valve system of claim 1, wherein the acidifying agent is covalently bound to the hydrogel.

11. The vascular valve system of claim 1, wherein the material layer spans a thickness of the valve along a longitudinal axis and is configured to fully cover a native valve when positioned between a body vessel and the vascular valve system.

12. The vascular valve system of claim 1, further comprising one or more acidic functionalities that are different than the calcium-chelating agent, wherein the acidic functionalities are configured to be positioned at an ion-exchange/calcified plaque interface.

* * * * *